United States Patent
Hutchinson (10) Patent No.: US 10,054,559 B2
(45) Date of Patent: Aug. 21, 2018

(54) COMPACT STEAM QUALITY AND FLOW RATE MEASUREMENT SYSTEM

(71) Applicant: Dan Hutchinson, Denver, CO (US)

(72) Inventor: Dan Hutchinson, Denver, CO (US)

( * ) Notice: Subject to any disclaimer, the term of this patent is extended or adjusted under 35 U.S.C. 154(b) by 105 days.

(21) Appl. No.: 15/223,841

(22) Filed: Jul. 29, 2016

(65) Prior Publication Data

US 2018/0031502 A1 Feb. 1, 2018

(51) Int. Cl.
  *G01N 25/60* (2006.01)
  *G01F 1/00* (2006.01)
  *G01N 25/00* (2006.01)

(52) U.S. Cl.
  CPC .............. *G01N 25/60* (2013.01); *G01F 1/00* (2013.01); *G01N 25/00* (2013.01)

(58) Field of Classification Search
  CPC ........... G01N 25/60; G01N 25/00; G01F 1/00
  See application file for complete search history.

(56) References Cited

U.S. PATENT DOCUMENTS

| | | | |
|---|---|---|---|
| 4,149,403 A | 4/1979 | Muldary et al. | |
| 4,832,503 A | 5/1989 | Dowling et al. | |
| 4,849,687 A | 7/1989 | Sims et al. | |
| 4,854,725 A | 8/1989 | Sims et al. | |
| 5,190,105 A | 3/1993 | D'Souza | |
| 5,307,833 A | 5/1994 | Stoy et al. | |
| 5,576,495 A | 11/1996 | Vetterick | |
| 5,845,386 A * | 12/1998 | Watts | F16L 23/032 285/179 |
| 5,869,771 A | 2/1999 | Rajan et al. | |
| 6,412,351 B1 | 7/2002 | Zunft | |
| 6,543,297 B1 | 4/2003 | Kleven | |
| 8,984,959 B2 | 3/2015 | Hutchinson | |
| 2002/0139197 A1 | 10/2002 | Salamitou et al. | |
| 2003/0074982 A1 | 4/2003 | Spielman | |
| 2003/0188586 A1 | 10/2003 | Orleskie et al. | |

(Continued)

OTHER PUBLICATIONS

J.C. Sims and D.H. Huthcinson, The Dielectric Steam Quality Sensor Laboratory Development and Field Evaluation, Society of Petroleum Engineers, 1997, pp. 23-35, SPE 37514, Society of Petroleum Engineers, US.

(Continued)

*Primary Examiner* — Son Le
*Assistant Examiner* — David Z Huang
(74) *Attorney, Agent, or Firm* — Leyendecker & Lemire, LLC (57) ABSTRACT

A compact, pressure conserving, steam quality and flow rate measurement system is described. Embodiments of the system can include a steam quality measuring device having a converging/diverging nozzle and a conditioning orifice plate. The steam quality measuring device can be adapted to measure flow conditions of a two-phase steam to determine steam quality. The converging/diverging nozzle can be implemented to reduce pressure loss and control flow rate. The conditioning orifice plate can be implemented to reduce flow conditioning pipe lengths and eliminate secondary flow conditioning elements. By placing the two flow elements in series, data from the flow elements can allow for a simultaneous solution of flow equations yielding a measurement for steam quality.

16 Claims, 10 Drawing Sheets

(56) References Cited

U.S. PATENT DOCUMENTS

2004/0221660 A1    11/2004    Dutton et al.
2014/0311251 A1    10/2014    Hutchinson

OTHER PUBLICATIONS

Suzanne Griston and Dan Hutchinson, Field Testing of Dielectric Steam Quality Sensor, Society of Petroleum Engineers, 1998, 12 pages, SPE 46236, Society of Petroleum Engineers, US.
Suzanne Castrup and Faisal Latif and Ali Al Kalbani, Tapered-Bean Steam Chokes Revisited, Society of Petroleum Engineers, 2011, 8 pages, SPE 144615-PP, Society of Petroleum Engineers, US.
Sze-Foo Chien, Predicting Wet-Steam Flow Regime in Horizontal Pipes, Journal of Petroleum Technology, Mar. 1990, pp. 356-362, Journal of Petroleum Technology, US.

\* cited by examiner

FIG. 9 ns system. The proportion of each phase at
COMPACT STEAM QUALITY AND FLOW RATE MEASUREMENT SYSTEM

BACKGROUND

Knowing or predicting flow regimes for wet steam flowing in a steam-distributing network is important to the engineering, management, and economics of steamflood enhanced oil recovery (EOR). All steam EOR systems involve a steam distribution system. Most steams used in oil field steam operations are a wet steam. More specifically, the steam can be classified as a two-phase flow including steam (vapor) and water (liquid). The proportion of each phase at a point in the distributions system can be affected by frictional pressure loss, liquid holdup, and unequal phase splitting at piping junctions. Phase splitting occurs when liquid water separates from the steam. The two phases have very different properties, including energy content. Defining the amount of each phase delivered to any point of consumption is important to the efficient and effective operation of oil recovery projects.

Consideration of an extent and a nature of mixing of the liquid and gas phases is critical to the accurate function of steam quality measuring systems. In multi-phase flows, these mixing conditions are referred to as flow regimes. Prior efforts to contend with the effects of flow regimes have mainly applied devices, such as flow straighteners or internal pipe baffling, to correct upstream flow conditions. However, the flow regime of two-phase flows can be unpredictable and render corrective mechanical devices largely ineffective, thereby producing inaccurate measurements.

DETAILED DESCRIPTION

Embodiments of the present invention can include a multi-phase steam quality and flow rate measurement system that can be implemented in an enhanced oil recovery system. The steam quality and flow rate measurement system can be coupled to a steam generator and one or more injectors of the enhanced oil recovery system. In one embodiment, the steam quality and flow rate measurement system can include, but is not limited to, a steam quality sensor assembly and a control module. In some instances, the steam quality sensor assembly can be located remotely from the control module.

Embodiments of the steam quality sensor assembly can include, but are not limited to, a pipe assembly having a conditioning orifice plate section and a phase mixing nozzle section. The phase mixing nozzle section can typically include, but is not limited to, a phase mixing nozzle and a pressure release assembly. The conditioning orifice plate section can generally include, but is not limited to, a first flange, a second flange, one or more seals or gaskets, and a conditioning orifice plate located between the flanges. In one instance, the pipe assembly can be a single pipe having a generally inverted "L" shape with a plurality of openings. In another instance, the pipe assembly can be comprised of multiple components forming a generally inverted "L" shape having a plurality of openings. In yet another instance, the pipe assembly can be a substantially straight piece of pipe having a plurality of openings.

Embodiments of the steam quality sensor assembly can eliminate a need for long upstream piping lengths and/or flow straightening/conditioning devices to normalize flow profile prior to measurement. Advantages of the steam quality sensor assembly include, but are not limited to, being uniquely compact, having minimum components, having minimum pressure drop, durability, low initial cost, and reduced maintenance. The steam quality sensor assembly can be retrofitted into existing enhanced oil recovery piping systems by having compact dimensions previously not possible.

As can be appreciated, a flow rate computation for mixed-phase steam through the nozzle and the conditioning orifice plate can be unique for each device. In both computations, there can be a common unknown variable, which is a ratio of the constituent phases or steam quality. With two unique equations sharing the same unknown variable, a simultaneous solution of those equations can allow for a determination of that unknown variable.

In one embodiment, the steam quality sensor assembly can include a pipe assembly designed to have the conditioning orifice plate and the phase mixing nozzle in-line. In such an embodiment, the pipe assembly can be substantially straight and include a flange assembly located proximate the phase mixing nozzle. The flange assembly can allow for easy access to the phase mixing nozzle. In one instance, the conditioning orifice plate can be located upstream from the phase mixing nozzle. In another instance, the phase mixing nozzle can be located upstream of the conditioning orifice plate.

In embodiments including the perpendicular configuration, the nozzle can be easily removed. For instance, an end cap can be opened and the nozzle can be unscrewed and extracted from inside the piping. As can be appreciated, a replacement nozzle with different dimensions can then be inserted and the end cap can be replaced. The perpendicular configuration can avoid any dis-assembly of the piping.

In embodiments having the in-line configuration and the perpendicular configuration, the systems can be relatively compact dimensionally when compared to prior art systems having concentric orifice plates. The systems can also provide a low pressure drop compared to prior art systems implementing straight bore chokes.

The phase mixing nozzle can be implemented to create two-phase flow regimes with zero slip, and vapor continuous phase, by intimately mixing the two-phase flow. A zero slip flow regime generally provides an accurate determination of an amount of vapor phase and liquid phase in steam.

Pressure and/or temperature sensors can be implemented to define conditions upstream and downstream of both the nozzle and the conditioning orifice plate. The measured conditions associated with the nozzle and the orifice plate can be used to calculate a steam quality and a flow rate. A pressure loss across a specific nozzle design, combined with the steam quality and one or more empirical parameters, can enable a determination of a total flow rate. Alternately, a pressure loss across a specific orifice plate design, combined with the steam quality and the one or more empirical parameters, can enable a determination of a total flow rate. In some embodiments, with consideration of operating conditions, the nozzle can be configured to control the steam flow rate.

In one embodiment, the multi-phase mixed flow can be directed in series through the conditioning orifice plate and the phase mixing nozzle. Both the phase mixing nozzle and the conditioning orifice plate may be removed and replaced as necessary. It is to be appreciated that the phase mixing nozzle or the conditioning orifice may be positioned in an upstream location. Static pressure located upstream and downstream of the nozzle can be measured by one or more pressure sensors and can be directed to the control module. Static pressure located upstream and downstream of the conditioning orifice plate can be measured by one or more pressure sensors and can be directed to the control module. As can be appreciated, a simultaneous solution of two flow equations, one for the nozzle and one for the conditioning orifice plate, can allow for a determination of the ratio of the two flowing phases to determine the steam quality.

Fully developed flow can generally have a symmetric velocity profile across a pipe section. Higher velocity flow can be centered on a longitudinal axis of the pipe section. In contrast, multi-phase fluid flow in a pipe section can be characterized by an asymmetric velocity profile across the pipe section. When an upstream pipe fitting, device, or flow regime skews the velocity profile, the pressure measured at a currently available concentric orifice flow meter pressure tap will be in error. A concentric orifice plate typically has a single concentric bore centered on a longitudinal axis of a pipe section.

A conditioning orifice plate can include a plurality of orifices arranged across a cross-section of the pipe section. Each of the plurality of orifices can conduct a part of the total fluid flow within the conduit. Each orifice may thereby serve an area of relatively high or low fluid velocity. According to Bernoulli's Theorem, a velocity of the fluid through each of the orifices will increase, and the static fluid pressure on the downstream side of the conditioning orifice plate that is attributable to each velocity region will be averaged into a single static pressure.

As can be appreciated, one method of defining a two-phase steam flow can be to measure steam quality. Steam quality can be defined as a ratio of a vapor phase flow rate divided by a total flow rate (e.g., vapor flow rate plus water flow rate). Previously known methods of measuring steam quality include using a long pipe run (e.g., 20 to 200 or more pipe diameters), a concentric orifice plate, and a straight bore critical flow choke having a 50% pressure drop or more. Using measurements from the orifice and the choke, a flow engineer can determine steam quality. By determining the steam quality in a given enhanced oil recovery system, the flow engineer can maximize the effectiveness of the steam introduced to an oil well.

For multi-phase flow applications, flow regimes prevail, and their affect must be accounted for. The conditioning orifice plate flow rate computation can account for flow regimes by including empirically derived parameters. A pressure loss across the conditioning orifice plate, steam quality, and the empirical parameter values enables a determination of a total flow rate. For a specific combination of the nozzle and the conditioning orifice plate, which define a certain range of flow conditions, the empirically derived parameters may be considered constant.

In one embodiment, the phase mixing nozzle can be implemented as a pressure recovery nozzle. The pressure recovery nozzle can allow for a conservation of system pressure by minimizing a loss of energy from a flowing fluid. In one instance, the pressure recovery nozzle can include a radiused entry, a converging section upstream of a minimum bore diameter, and a diverging section downstream of the minimum bore diameter. By virtue of this geometry, flow velocity can be both increased and then reduced in a controlled manner, efficiently converting kinetic energy to potential energy. An overall pressure loss through the nozzle can thereby be minimized.

When the velocity of the fluid in the minimum bore area section exceeds sonic velocity, the flow condition can be referred to as "critical flow." During "critical flow," the flow rate can remain constant despite a decrease in downstream pressure. With consideration of operating conditions, a size of the nozzle can be selected to act as a flow control device for the steam flow rate. In one instance, a nozzle may be selected to provide a critical flow. In another instance, the nozzle can be selected to provide a sub-critical flow. Sub-critical flow rates can be calculated by first assuming a critical flow, then using an empirically derived correction and applying the correction to the critical flow rate computation.

The flow rate through the nozzle can be affected by a flow regime in a similar fashion to the effect flow regimes have on the conditioning orifice plate. To account for flow regime effects, the nozzle flow rate computation can include empirically derived parameters. For a specific combination of the nozzle and the conditioning orifice plate, defining a range of flow conditions, the empirically derived parameter values may be considered constant.

A simultaneous solution of the two flow equations, including the empirical parameters, and an iterative methodology, allows a determination of the total flow rate and a ratio of the phases resulting in a steam quality measurement.

Terminology

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning either or both.

References in the specification to "one embodiment", "an embodiment", "another embodiment", "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "couple" or "coupled" as used in this specification and appended claims refers to an indirect or direct physical connection between the identified elements, components, or objects. Often the manner of the coupling will be related specifically to the manner in which the two coupled elements interact.

The term "directly coupled" or "coupled directly," as used in this specification and appended claims, refers to a physical connection between identified elements, components, or objects, in which no other element, component, or object resides between those identified as being directly coupled.

The term "approximately," as used in this specification and appended claims, refers to plus or minus 10% of the value given.

The term "about," as used in this specification and appended claims, refers to plus or minus 20% of the value given.

The terms "generally" and "substantially," as used in this specification and appended claims, mean mostly, or for the most part.

Directional and/or relationary terms such as, but not limited to, left, right, nadir, apex, top, bottom, upstream, downstream, vertical, horizontal, back, front and lateral are relative to each other and are dependent on the specific orientation of an applicable element or article, and are used accordingly to aid in the description of the various embodiments and are not necessarily intended to be construed as limiting.

The term "software," as used in this specification and the appended claims, refers to programs, procedures, rules, instructions, and any associated documentation pertaining to the operation of a system.

The term "firmware," as used in this specification and the appended claims, refers to computer programs, procedures, rules, instructions, and any associated documentation contained permanently in a hardware device and can also be flashware.

The term "hardware," as used in this specification and the appended claims, refers to the physical, electrical, and mechanical parts of a system.

The terms "computer-usable medium" or "computer-readable medium," as used in this specification and the appended claims, refers to any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium. By way of example, and not limitation, computer readable media may comprise computer storage media and communication media.

The term "signal," as used in this specification and the appended claims, refers to a signal that has one or more of its characteristics set or changed in such a manner as to encode information in the signal. It is to be appreciated that wireless means of sending signals can be implemented including, but not limited to, Bluetooth, Wi-Fi, acoustic, RF, infrared and other wireless means.

An Embodiment of a Steam Quality Measurement System

Figure 1:
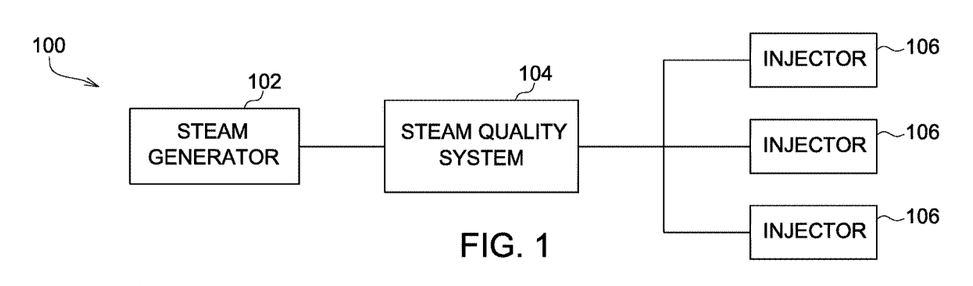
FIG. 1 is a block diagram of an enhanced oil recovery system according to one embodiment of the present invention.

Referring to FIG. 1, a block diagram of an embodiment 100 showing an enhanced oil recovery system is illustrated. The enhanced oil recovery system 100 includes means of thermally affecting an oil reserve. By thermally affecting the oil reserve, a higher percentage of oil recovery can be achieved in some instances.

Generally, the enhanced oil recovery system 100 includes a steam generator 102, a steam quality system 104, and one or more injectors 106. The injectors 106 can be adapted to deliver steam to an oil reserve. In one embodiment, the steam generator 102 can be powered by fossil fuels. It is to be appreciated that other means of generating steam can be implemented including, but not limited to, solar powered steam generators.

Steam generated by the steam generator 102 can be channeled to the steam quality system 104 before being routed to the injectors 106 to be delivered to an oil reserve. The steam quality system 104 can be configured to collect data used to determine the quality of the steam generated by the steam generator 102. In one embodiment, data measured by the steam quality system 104 can be used by an engineer to determine how to control an overall flow rate of the system 100.

Figure 2:
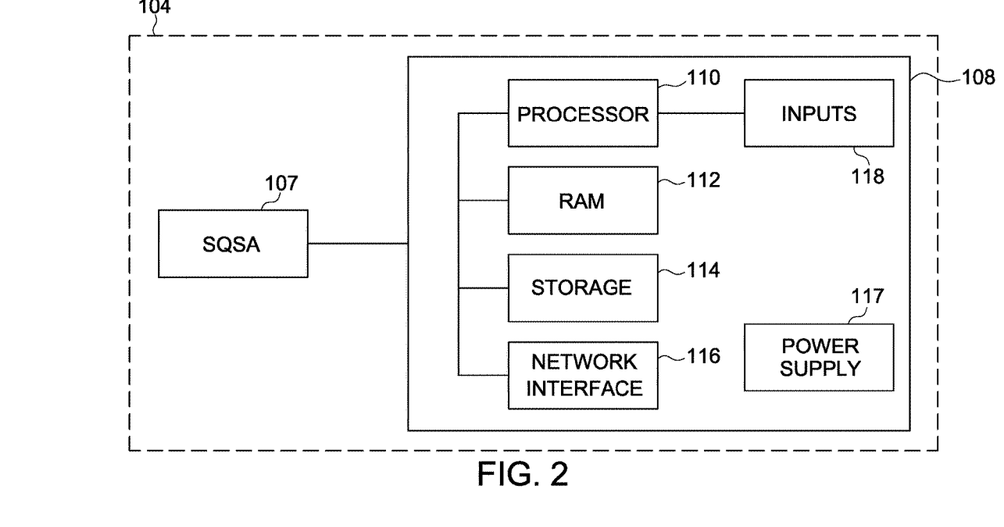
FIG. 2 is block diagram of a steam quality system according to one embodiment of the present invention.

Referring to FIG. 2, a block diagram of the steam quality system 104 is shown. Generally, the steam quality system 104 can include a steam quality sensor assembly 107 and a control module 108.

The control module 108 can include a processor 110, a random access memory 112, and a nonvolatile storage 114 (or memory), as shown in FIG. 2. The processor 110 can be a single microprocessor, multi-core processor, or a group of processors. The random access memory 112 can store executable code as well as data that may be immediately accessible to the processor 110, while the nonvolatile storage 114 can store executable code and data in a persistent state.

The control module 108 can also include a network interface 116. The network interface 116 can include hard-wired and wireless interfaces through which the control module 108 can communicate with other devices. For example, the control module 108 can wirelessly interface with a computing device used by an oil field engineer. In another example, the control module 108 can wirelessly interface with one or more sensors of the steam quality sensor assembly 107.

Generally, the controller can include a power supply 117. In one embodiment, the power supply 117 can be a battery charged by converted solar energy. It is to be appreciated that other means of powering the control module 108 can be implemented. For instance, a pre-charged battery can be implemented to power the control module 108.

One or more inputs 118 can be included as part of the control module 108 to receive signals from sensors associated with the steam quality sensor assembly 107. For example, a pressure sensor in the steam quality sensor assembly 107 can send pressure readings via a signal to the control module 108. Some embodiments of the present invention can include a wireless interface between the control module 108 and various sensors.

The controller 108 can be adapted to calculate a steam quality based on information received from the steam quality sensor assembly 107. For example, based on signals received from the sensors, including static pressure and differential pressure, and using pre-determined empirical parameters, the controller 108 can calculate or measure steam quality. In one embodiment, the network interface 116 can send a signal containing the calculated steam quality to a remote location. For instance, a real-time steam quality measurement can be sent to an engineer in charge of overseeing the enhanced oil recovery system 100. In another embodiment, the memory 114 can be adapted to store real time steam quality measurements for later retrieval by an engineer.

Pressure and/or temperature sensors can be used to define steam quality conditions in the steam quality sensor assembly 107. For instance, properties of saturated vapor and liquid phase upstream and downstream of a nozzle in the steam quality sensor assembly 107 can be used to calculate steam quality and flow rate. Total flow rate can be calculated based on steam quality, empirically derived parameter values, and pressure loss across either a nozzle or an orifice plate in the steam quality sensor assembly 107.

Figure 3:
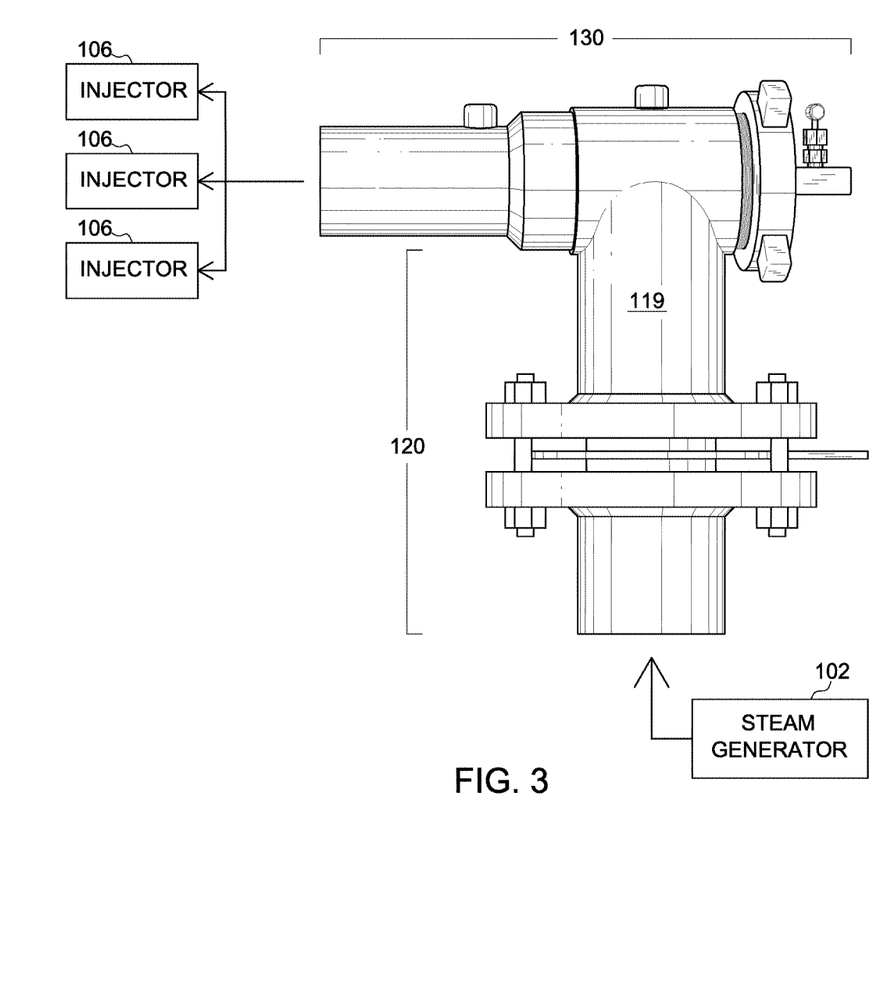
FIG. 3 is a side view of a steam quality measurement device according to one embodiment of the present invention.

Referring to FIG. 3, a detailed diagram of a steam quality sensor assembly 107 is illustrated. As shown, the steam quality sensor assembly 107 can include an opening or orifice adapted to receive steam from the steam generator 102. As steam passes through the steam quality sensor assembly 107, the steam can exit via another opening or orifice and continue on to the injectors 106. In one embodiment, all steam generated by the steam generator 102 can be channeled to the steam quality sensor assembly 107 and then on to the injectors 106. It is to be appreciated that less than 100% of steam generated by the steam generator 102 can be channeled through the steam quality system 104 for testing steam quality. For example, 20% of steam generated can be directed through the steam quality system 104 for testing purposes.

As shown in FIG. 3, the steam quality sensor assembly 107 can typically include a pipe assembly 119 having a conditioning orifice plate section 120 and a phase mixing nozzle section 130.

Figure 4A:
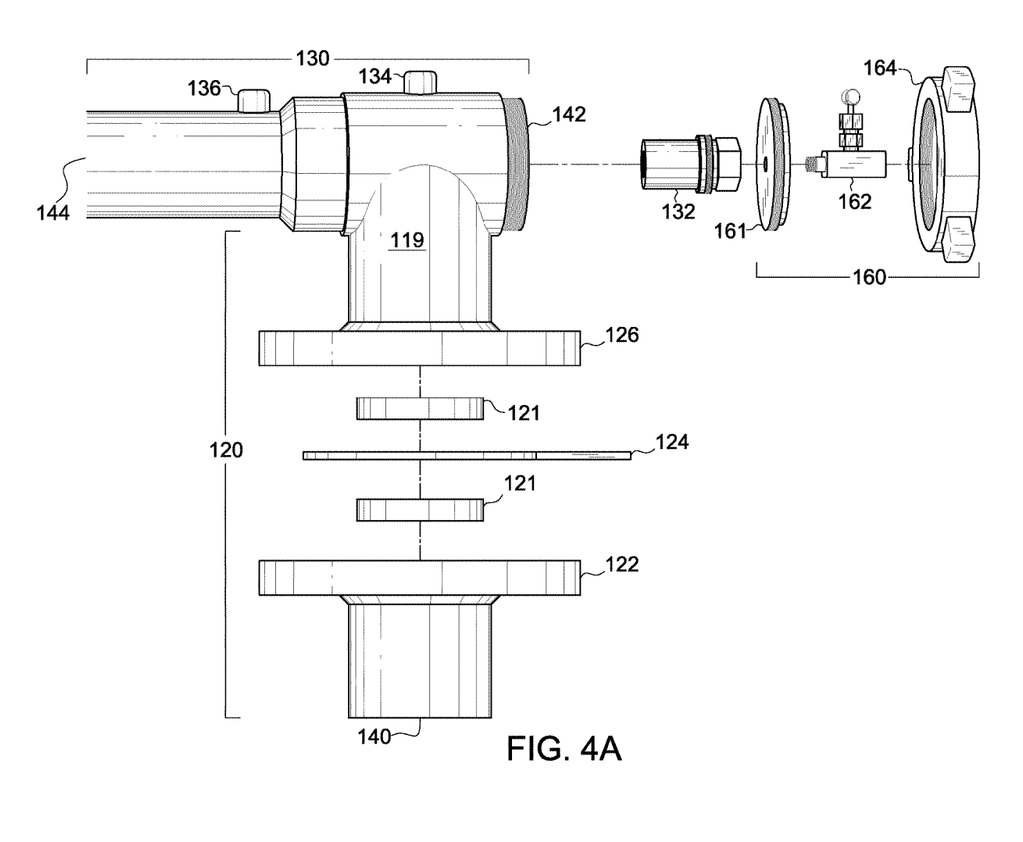
FIG. 4A is an exploded view of a steam quality measurement device according to one embodiment of the present invention.

Referring to FIG. 4A, an exploded view of the pipe assembly 119 is illustrated. As shown, the conditioning orifice plate section 120 can include, but is not limited to, a first flange 122, a plate 124, and a second flange 126. As will be discussed hereinafter, the plate 124 can typically include one or more orifices 128 and the flanges 122, 124 can each include a sensor port. Typically, a seal or gasket 121 can be placed between the first flange 122 and the plate 124 and between the plate 124 and the second flange 126. It is to be appreciated that other means of sealing the interface between the plate 124 and the flanges 122, 126 are contemplated. In one embodiment, the seals 121 can each be a high temperature pressure seal or gasket. The seals 121 can be adapted to sustain repeated removal and replacement of the plate 124. For instance, the seals 121 can be adapted to facilitate an initial installation of the plate 124 and subsequent removal, resizing, and replacement of the plate 124 to accommodate changes in the enhanced oil recovery system 100 evolving over a life of the system.

Typically, the conditioning orifice plate 124 can be accessed by uncoupling the first flange 122 and the second flange 126. As can be appreciated, the conditioning orifice plate 124 can be replaced as needed. The flanges 122, 126 provide a quick and easy access point for providing maintenance and/or replacing the plate 124.

The phase mixing nozzle section 130 can generally include, but is not limited to, a nozzle 132, a first sensor port 134, a second sensor port 136, and a pressure release assembly 160.

The pipe assembly 119 can include, but is not limited to, a first orifice or opening 140, a second orifice or opening 142, and a third orifice or opening 144. The first orifice 140 can be adapted to receive steam from the steam generator 102. The second orifice 142 can be adapted to receive the nozzle 132 and the pressure release assembly 160. The third orifice 144 can be an outlet for the steam from the steam generator 102.

In one embodiment, the first opening 140 can be an inlet port and the third opening 144 can be an outlet port. The inlet port 140 can be adapted to receive steam from the steam generator 102 and direct steam through the conditioning orifice plate section 120 towards the nozzle section 130. The outlet port 144 can be adapted to direct steam out of the pipe assembly 119. In one embodiment, the inlet port 140 can be oriented orthogonally to the outlet port 144. Depending on an implementation, the length of each of the ports 140, 144 can be increased or decreased. In one embodiment, the inlet port 140 and the outlet port 144 can each be threaded. In another embodiment, the inlet port 140 and the outlet port 144 can have flanged connections. It is to be appreciated that other means of connecting the ports to piping of the enhanced oil recovery system 100 can be implemented.

Figure 5:
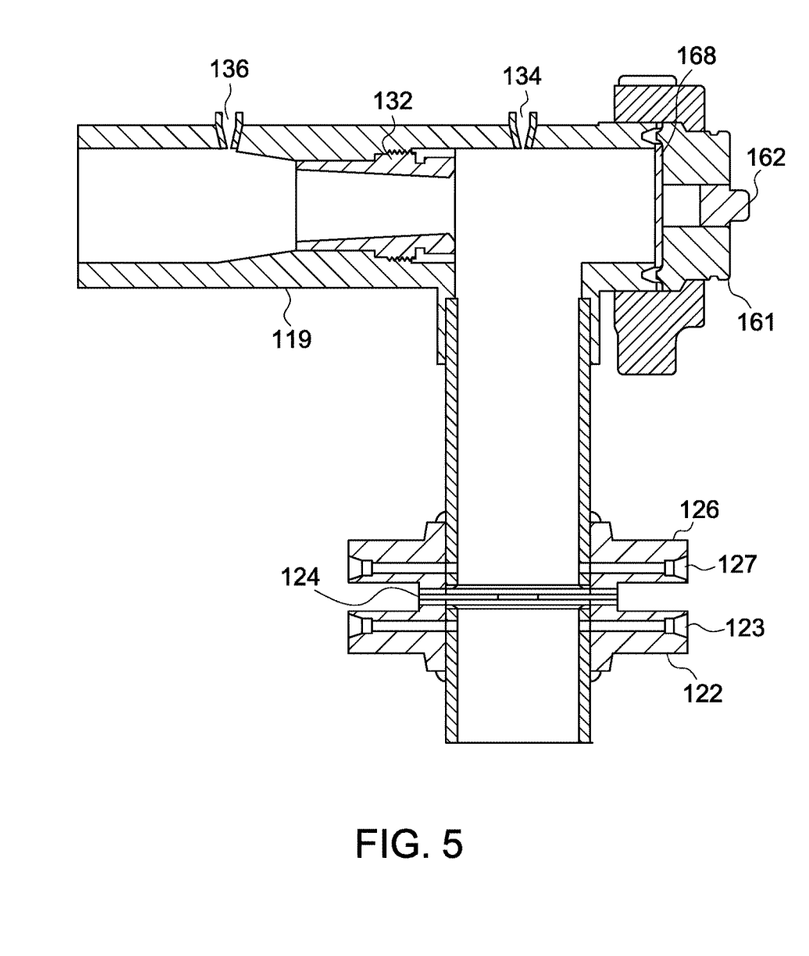
FIG. 5 is a cross-sectional view of a steam quality measurement device according to one embodiment of the present invention.

The phase mixing nozzle section 130 can include the first sensor port 134 and the second sensor port 136 for receiving one or more sensors. Generally, the first sensor port 134 can be located upstream of the nozzle 132 and the second sensor port 136 can be located downstream of the nozzle 132, as shown in FIGS. 4A and 5. The first sensor port 134 and the second sensor port 136 can each be adapted to receive and couple to one or more sensors. For instance, the first sensor port 134 can couple to a pressure sensor and the second port 136 can couple to a temperature sensor. In another instance, the first sensor port 134 can couple to a temperature sensor and the second sensor port 136 can couple to a pressure sensor. It is to be appreciated that other types of sensors are contemplated and can be implemented to take measurements.

Figure 4B:
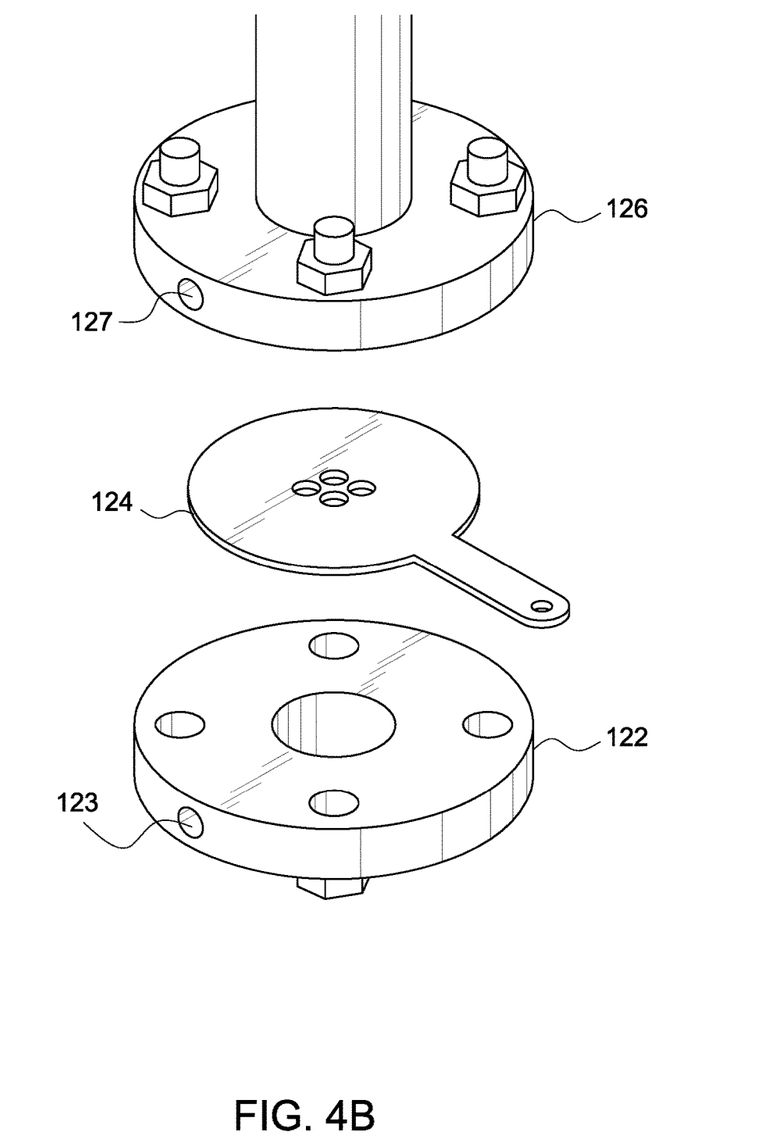
FIG. 4B is an exploded view of a conditioning orifice plate section according to one embodiment of the present invention.

Referring to FIG. 4B, a detailed diagram of the conditioning orifice plate section 120 is illustrated. As shown, the first flange 122 can include a sensor port 123 and the second flange 126 can include a sensor port 127. Generally, the first flange sensor port 123 can be located upstream of the conditioning orifice plate 124 and the second flange sensor port 127 can be located downstream of the conditioning orifice plate 124. Similar to the sensor ports 134, 136 of the nozzle section 130, the flange sensor ports 123, 127 can be adapted to receive and couple to one or more sensors. For instance, the first flange sensor port 123 can couple to a pressure sensor and the second flange sensor port 127 can couple to a temperature sensor. In another instance, the first flange sensor port 123 can couple to a temperature sensor and the second flange sensor port 127 can couple to a pressure sensor. It is to be appreciated that other types of sensors are contemplated that can be implemented to take measurements. As can be appreciated, sensors located in the sensor ports can be connected to the inputs 118 of the remote module 108 and in communication with the remote module 108.

In one embodiment, the conditioning orifice plate can include a plurality of orifices arranged across a cross-section of an internal cavity of the conditioning orifice plate section 120, as shown in FIGS. 7A-7D. As can be appreciated, each of the plurality of orifices can conduct a part of a total fluid flow within the pipe conduit. Each orifice may thereby serve an area of (relatively) high or low fluid velocity. According to Bernoulli's Theorem, a velocity of the fluid through each of the orifices will increase, and a static fluid pressure on the downstream side of the constricting plate that is attributable to each velocity region can be averaged into a single static pressure.

Referring to FIG. 5, a cross-sectional view of the steam quality sensor assembly 107 is illustrated. As shown, a bore of the nozzle 132 can be oriented substantially perpendicular to orifices of the conditioning orifice plate 124. As can be appreciated, as steam passes through the sensor assembly 107 the steam can first pass through the conditioning orifice plate 124 and then pass through the nozzle 132. In some embodiments, the nozzle 132 can be located upstream of the conditioning orifice plate 124. For instance, steam can pass through the nozzle 132 first and then pass through the conditioning orifice plate 124 when passing through the sensor assembly 107.

In one embodiment, as shown in FIGS. 3-5, steam can pass through the conditioning orifice plate 124 in a first direction and then the steam can be channeled approximately 90 degrees in another direction and then pass through the nozzle 132.

In some embodiments, the sensor assembly 107 can include the pressure release assembly 160. The pressure release assembly 160 can include a mounting 161 and a device 162 adapted to control release of steam pressure inside the sensor assembly 107. For example, the pressure release device 162 can include, but is not limited to, a threaded relief plug, a valve, and/or other devices adapted to vent or release steam pressure. The pressure release device 162 can couple to the mounting 161. For example, the pressure release device 162 can be threadably engaged with the mounting 161. The pressure release device 162 can be coupled to an end cap 164 via the mounting 161. The end cap 164 can be removably coupled to sensor assembly 107. Generally, the end cap 164 is removably coupled approximate the second orifice 142 of the sensor assembly 107.

The pressure release end cap 164 can include a seal 168. In one embodiment, the seal 168 can be a high temperature pressure seal or gasket. The seal 168 can be adapted to sustain repeated removal and replacement of the end cap 164. For instance, the seal 168 can be adapted to facilitate an initial installation of the nozzle 132 and subsequent removal, resizing, and replacement of the nozzle 132 to accommodate changes in the enhanced oil recovery system 100 evolving over a life of the system.

Figure 6A:
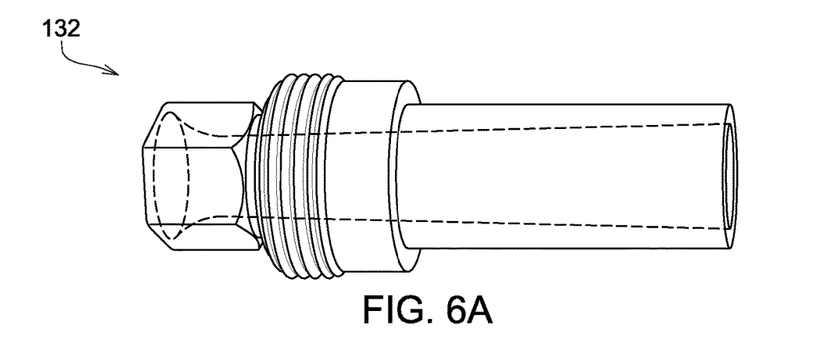
FIG. 6A is a side view of a nozzle according to one embodiment of the present invention.
Figure 6B:
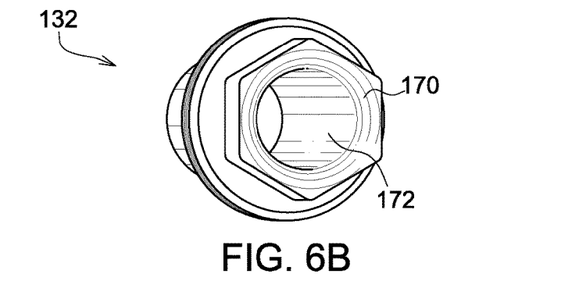
FIG. 6B is a top view of a nozzle according to one embodiment of the present invention.
Figure 6C:
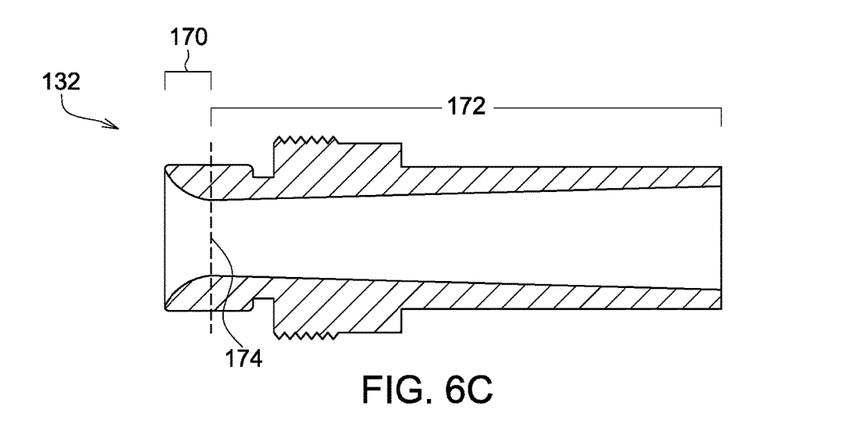
FIG. 6C is a cross-sectional view of a nozzle according to one embodiment of the present invention.

Referring to FIGS. 6A-6C, detailed diagrams of one embodiment of the nozzle 132 are shown. FIG. 6A is a side view of one embodiment of the nozzle 132 showing the interior bore converging and diverging. FIG. 6B is a top view of the nozzle 132 showing a converging portion of the nozzle 132. FIG. 6C is a cross-sectional view of the nozzle 132.

In one embodiment, the nozzle 132 can be a converging/diverging nozzle or de Laval nozzle. The converging/diverging nozzle 132 can produce optimum mixing characteristics with minimal pressure loss. It is to be appreciated that the nozzle 132 can be a constant bore choke or nozzle, or other flow restricting device sized and shaped to create a desired mixing of the two-phase flow, as specified herein.

In addition to mixing, measurement of a pressure drop across the nozzle 132 can be combined with a steam quality measurement to compute a mass flow rate of the two-phase steam, and a total steam mass flow rate. Generally, a pressure drop across the nozzle 132 of up to 15% allows flow measurement, while greater pressure drops also allow flow control. It is to be appreciated that the pressure drop can be increased or decreased depending on certain conditions of the enhanced oil recovery system 100.

As shown in FIGS. 5-6C, an internal diameter of the nozzle 132 diverges or increases as the two-phase steam flows downstream toward the injector. In one embodiment, the diameter of the nozzle 132 can reach an interior diameter of the pipe assembly 119. By converging and then quickly diverging the bore of the nozzle 132, the nozzle 132 can mix the two-phase flow to generate a vapor continuous flow regime and to recover pressure loss by converting kinetic energy back to potential energy.

As shown generally in FIGS. 6B-6C, a converging portion 170 of the converging/diverging nozzle 132 can be upstream of a diverging portion 172. A constant diameter throat 174 of the nozzle 132 is generally located approximate an end having the converging portion 170. The throat 174 can be a portion of the nozzle 132 with the smallest cross-section (or diameter). The throat 174 can be located approximate where the nozzle 132 changes from converging to diverging. Generally, the converging portion 170 is smaller in length than the diverging portion 172 relative to an overall length of the nozzle 132. For example, for a nozzle having a 4 inch length, the converging portion can be a ¼ of an inch long and the diverging portion can be 3 and ½ inches long. The straight minimum bore diameter section 174 can be ¼ of an inch long, separating the converging and diverging portions. It is to be appreciated that the size or length of the converging portion 170, the diverging portion 172, and the constant dimension minimum bore section 174 can be altered.

In one embodiment, a length of the nozzle 132 can be four inches. In another embodiment, the length of the nozzle 132 can be three inches. It is to be appreciated that a length of the nozzle 132 can be varied depending on a specific implementation and requirement of an enhanced oil recovery system.

A diameter of the throat 174 can be adjusted based on a specific implementation of the nozzle 132. For example, a diameter of the throat can vary from three-eighths of an inch (0.375") to one and three-eighths of an inch (1.375").

The diverging portion 172 of the nozzle 132 can act as a diffuser that decelerates velocity and increases pressure of the two-phase steam. In one embodiment, the diverging portion 172 can have a six degree (6°) tapered-bore angle. The 6° tapered-bore angle can increase pressure recovery as the two-phase steam enters and exits the nozzle 132. In some instances, the 6° tapered-bore angle can reduce flow separation from the tapered wall, further reducing pressure loss. In some embodiments, an interior of the pipe assembly 119 approximate the nozzle 132 can be machined to extend the taper downstream of the nozzle 132, as shown in FIG. 5.

Generally, the converging/diverging nozzle 132 can mix the two-phase flow in the converging portion 170. In the diverging portion 172, the nozzle 132 can recover energy by tapering outwards at a controlled rate. The outward taper can reduce turbulent flow conditions, which can minimize energy loss. In one embodiment, the nozzle 132 can be a "quiet nozzle," where energy loss is minimized while still mixing the two-phase flow.

In one embodiment, the nozzle 132 can be a positive choke having a fixed orifice and being removably coupled to the pipe assembly 119. As shown in FIG. 5, the nozzle 132 can be located downstream from the conditioning orifice plate 124. Generally, the nozzle 132 can be coupled to an interior of the pipe assembly 119. For instance, the nozzle 132 can be threadably engaged with the pipe assembly 119. In one example, the nozzle 132 can be removably engaged with the pipe assembly 119. It is to be appreciated that a variety means of coupling the nozzle 132 to the pipe assembly 119 can be implemented without exceeding the scope of this disclosure.

In some embodiments, the nozzle 132 can function as a steam flow regulating and control device. By controlling a pressure drop and critical flow conditions, the nozzle 132 can limit flow through the enhanced oil recovery system 100.

In one embodiment, the pipe assembly 119 of the steam quality sensor assembly 107 can be manufactured from several different components. For instance, the pipe assembly 119 can typically include a pipe tee coupled to a pipe having a flanged coupling, and a pipe connected to one junction of the pipe tee. In one example, the components of the pipe assembly 119 can be removably coupled to one another. For example, the pipe tee can be threadably coupled to a pipe housing the nozzle 132. In one embodiment, the pipe assembly 119 can be manufactured as one pipe.

Figures 7A, 7B, 7E:
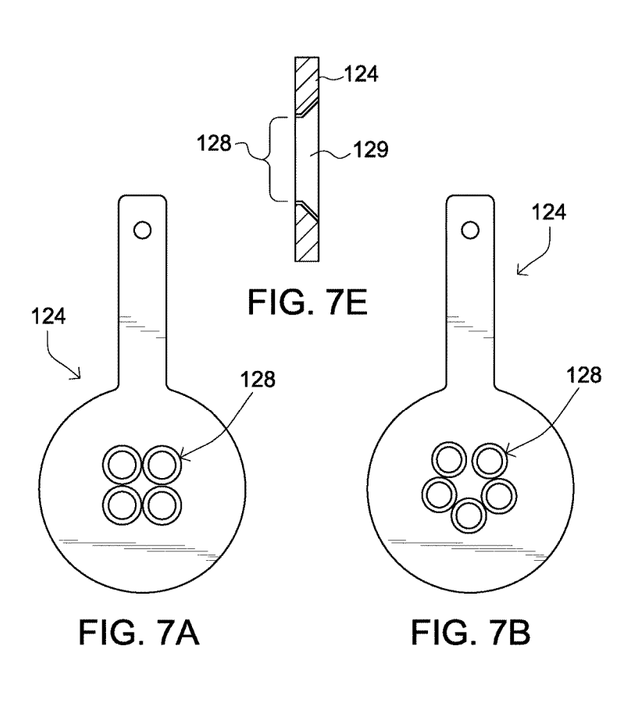
FIGS. 7A-7D include front views of several different conditioning orifice plates according to one embodiment of the present invention.
FIG. 7E is a cross-sectional view of an orifice bore of a conditioning orifice plate according to one embodiment of the present invention.
Figure 7C:
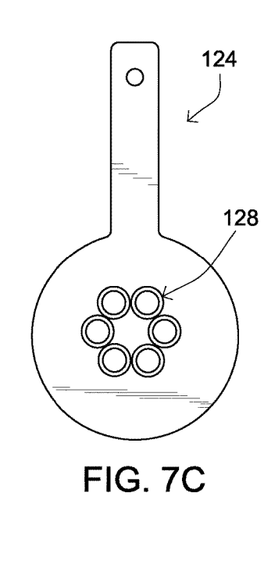
Figure 7D:
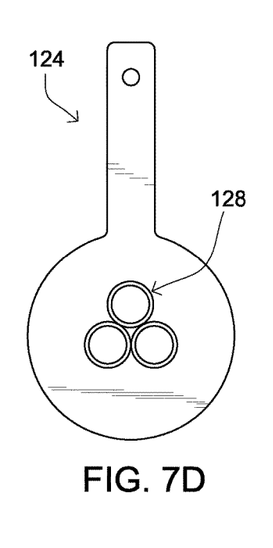

Referring to FIGS. 7A-7D, a plurality of different configurations for the conditioning orifice plate 124 are illustrated. Typically, the conditioning orifice plate 124 can include a plurality of orifices 128. In one embodiment, as shown in FIG. 7A, the conditioning orifice plate 124 can include four circular orifices arranged in a square. As shown in FIG. 7B, the conditioning orifice plate 124 can include five circular orifices arranged in a circle. As shown in FIG. 7C, the conditioning orifice plate 124 can include six circular orifices arranged in a circle. As shown in FIG. 7D, the conditioning orifice plate 124 can include three orifices arranged in a triangle. It is to be appreciated that the conditioning orifice plates 124 illustrated in FIGS. 7A-7D are for illustrative purposes only, and not meant to be limiting. In some instances, design parameters for the conditioning orifice plate 124 can be dictated by a set-up of an enhanced oil recovery system the conditioning orifice plate 124 will be implemented in.

Referring to FIG. 7E, a cross-sectional view of a bore 129 of one of the plurality of orifices 128 is illustrated. As shown, the orifice bore 129 can be chamfered. In one embodiment, the conditioning orifice plate 124 can be oriented such that the chamfer is oriented downstream. Stated alternatively, the bore 129 can be tapered in a downstream direction. For instance, a wider portion of the tapered bore 129 can be located upstream. In one embodiment, the orifice bore 129 can converge along a length of the bore.

Figure 8A:
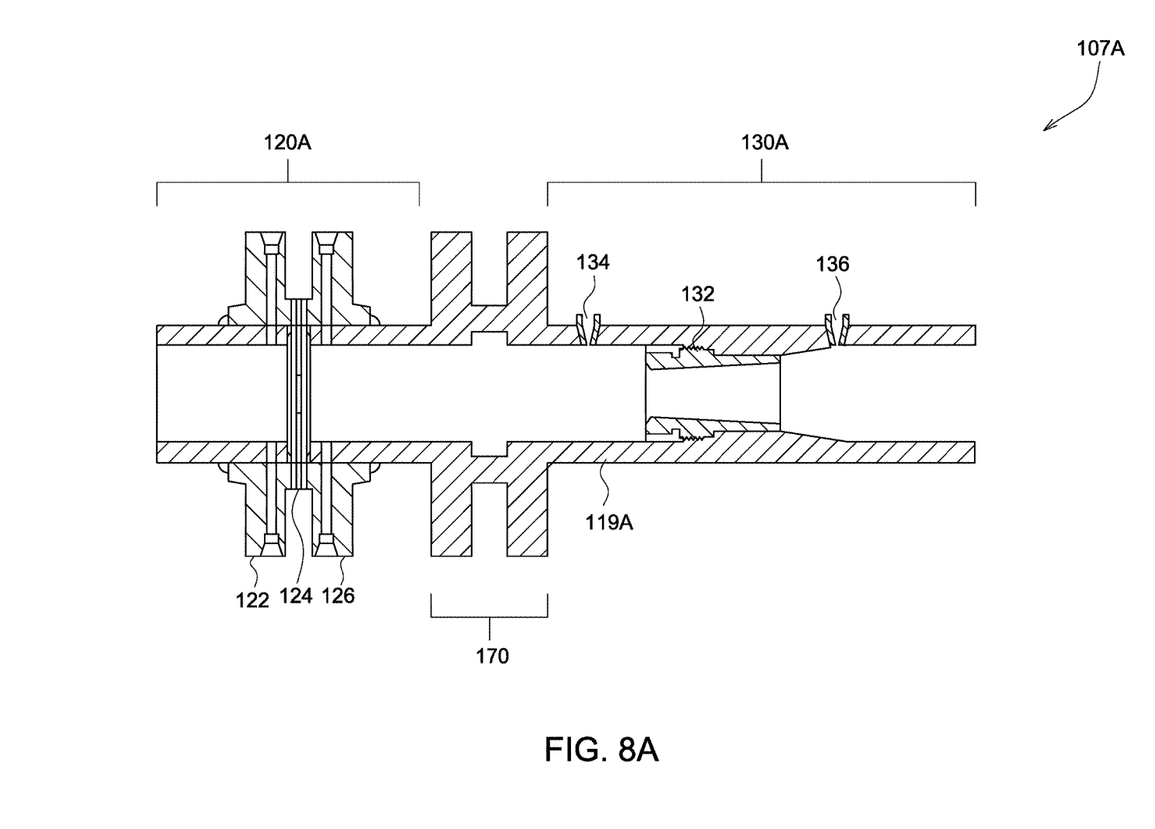
FIG. 8A is a cross-sectional view of a steam quality measurement device according to one embodiment of the present invention.

Referring to FIG. 8A, a second embodiment 107A of the steam quality sensor assembly is illustrated. As shown, the steam quality sensor assembly 107A can include components similar to the first embodiment steam quality sensor assembly 107. Of note, the second embodiment sensor assembly 107A can be configured with the conditioning orifice plate 124 and a bore of the nozzle 132 being in line with one another.

Generally, the second embodiment steam quality sensor assembly 107A can include a pipe assembly 119A having a conditioning orifice plate section 120A and a phase mixing nozzle section 130A. As shown, the conditioning orifice plate 124 can be located upstream of the nozzle 132, similar to the first embodiment steam quality sensor assembly 107.

The sensor assembly 107A can further include a flange assembly 170 for accessing the phase mixing nozzle 132. As shown, the flange assembly 170 can be located proximate the phase mixing nozzle 132. As can be appreciated, to remove, replace, or change the phase mixing nozzle 132, a user can separate the flange assembly 170 and access the phase mixing nozzle 132. Having access to the phase mixing nozzle 132 allows a user to efficiently and effectively implement a properly sized nozzle in the sensor assembly 107A.

Figure 8B:
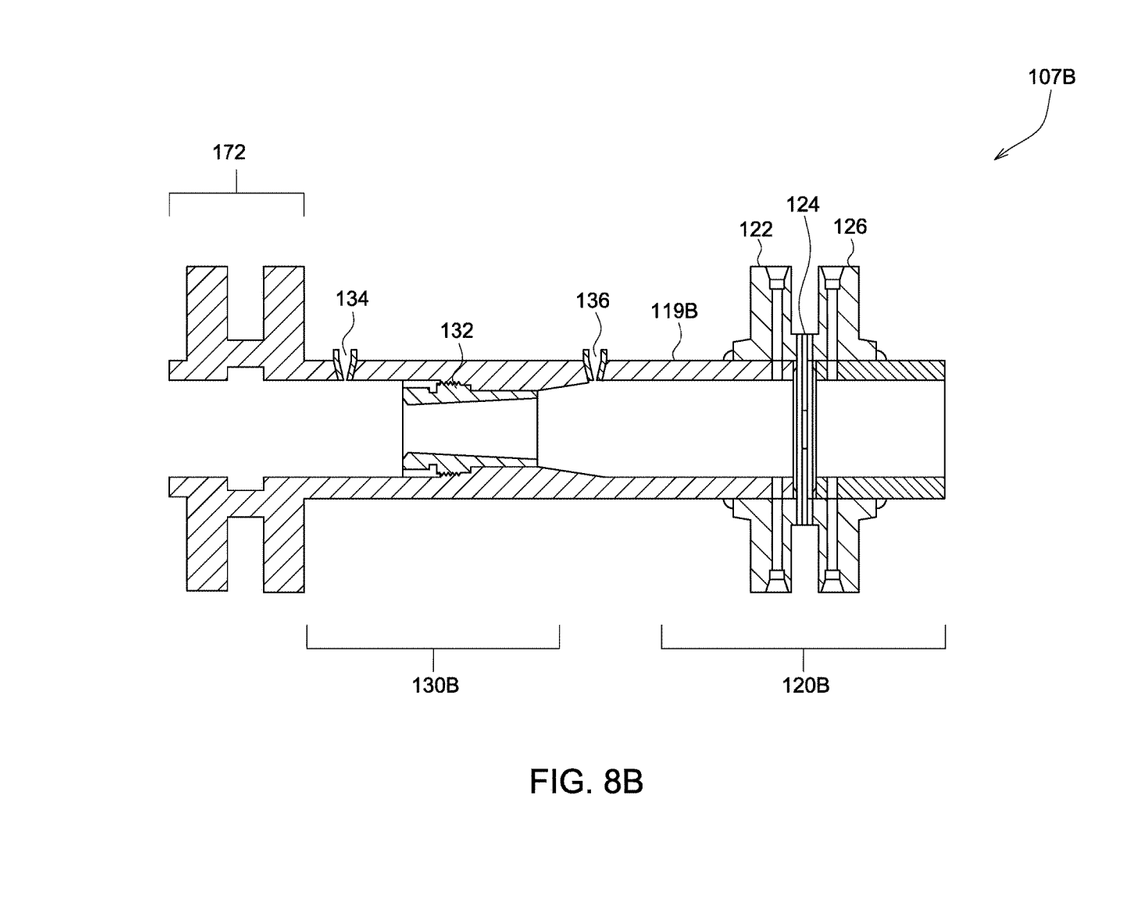
FIG. 8B is a cross-sectional view of a steam quality measurement device according to one embodiment of the present invention.

Referring to FIG. 8B, a third embodiment 107B of the steam quality sensor assembly is illustrated. The third embodiment sensor assembly 107B can include components similar to the first embodiment sensor assembly 107 and the second embodiment sensor assembly 107A.

As shown, the third embodiment sensor assembly 107B can include a pipe assembly 119B having a conditioning orifice plate section 120B, a phase mixing nozzle section 130B, and a flange assembly 172. Of note, the phase mixing nozzle 132 can be located upstream of the conditioning orifice plate 124. Similar to the flange assembly 170 of the second embodiment sensor assembly 107A, the flange assembly 172 can be implemented to provide access to the nozzle 132.

A Method of Sizing a Nozzle for a Steam Quality Measurement System

Figure 9:
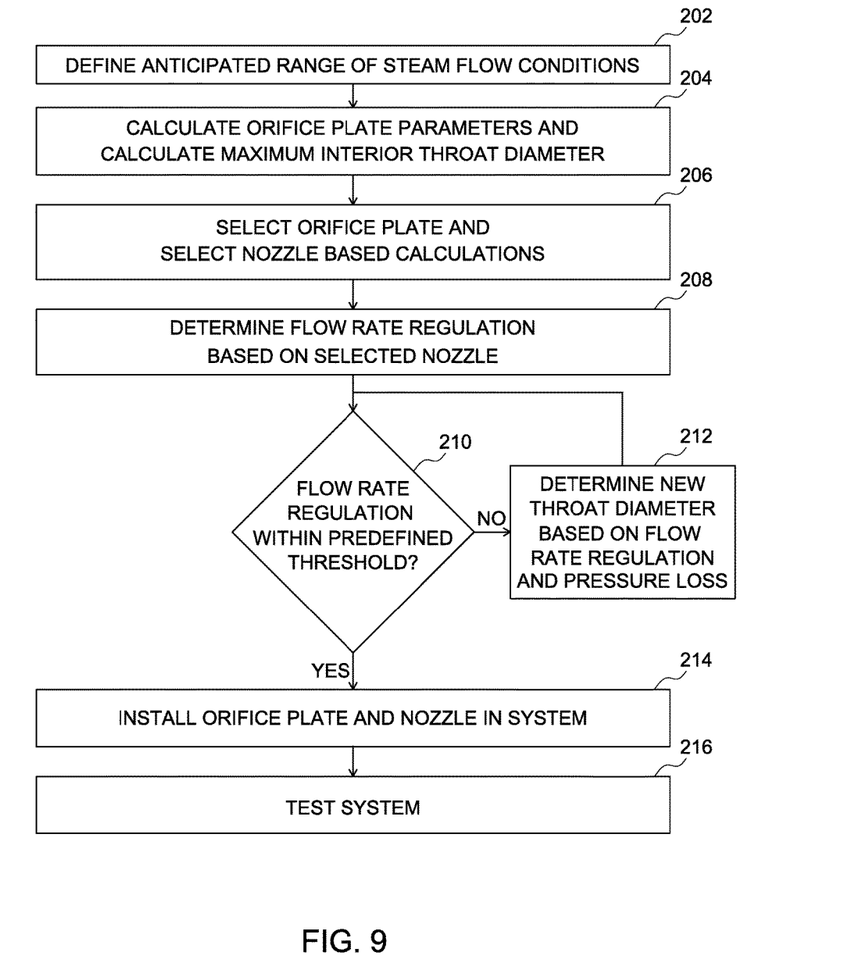
FIG. 9 is a flow diagram illustrating a method according to one embodiment of the present invention.

Referring to FIG. 9, a flow chart illustrating a method or process 200 for designing a nozzle and a conditioning orifice plate for implementation in the steam quality measurement system 100 is shown. Depending on a variety of factors, nozzles having different sized throat diameters and differently designed conditioning orifice plates can be implemented in the steam quality measurement system. Design parameters of a conditioning orifice plate including, but not limited to, orifice bore size, number of orifices, and configuration of the orifices can be determined on a case by case basis.

In block 202, an anticipated range of steam flow conditions of an enhanced oil recovery system can be defined. Steam flow conditions can include, but are not limited to, system pressure, steam mass flow rates, and steam quality ranges. Generally, the flow conditions can be defined prior to installation of the steam quality measurement system.

Based on the defined steam flow conditions, a maximum interior throat diameter of a nozzle and design parameters of a conditioning orifice plate can be computed in block 204.

In block 206, a nozzle can be selected with a throat diameter approximate in size with the computed throat diameter and a conditioning orifice plate with design parameters approximate in configuration with the computed design parameters. As can be appreciated, the larger the nozzle throat diameter is, the less pressure is lost.

In block 208, flow rate regulation can be determined based on the selected nozzle. Flow rate regulation can be achieved when a velocity of a flow reaches sonic velocity. At sonic velocity, critical flow is achieved which can produce a constant flow rate.

The process 200 can then move to block 210 to determine if the flow rate is within a predefined threshold. If the flow rate is outside the predefined threshold, the process 200 can move to block 212. If the flow rate is within a predefined threshold, the process 200 can move to block 214.

In block 212, a new throat diameter size can be determined based primarily on flow rate regulation factors and secondarily on pressure loss. For example, increased pressure loss can be traded for better flow rate regulation. The process 200 can move back to block 210 to determine if the flow rate is within the predefined threshold. If the flow rate regulation is acceptable, the system can move to block 214.

In block 214, the nozzle and the conditioning orifice plate can be installed in the steam quality measurement system.

In block 216, live testing of the steam quality measurement system can be conducted to make sure the selected components are working as predicted.

Alternative Embodiments and Variations

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

I claim:

1. A steam quality measurement system comprising:
   a sensor assembly including:
   an inlet adapted to receive a two-phase flow;
   a removable plate including one or more orifices each having a bore, the removable plate adapted to condition the two-phase flow;
   a removable nozzle having a bore, wherein the bore of the removable nozzle is oriented substantially perpendicular to each respective bore of the one or more orifices of the removable plate; and
   an outlet adapted to discharge the two-phase flow;
   a control module adapted to calculate a steam quality of the two-phase flow based on information received from the sensor assembly;
   wherein the two-phase flow is adapted to be directed through the one or more orifices and the nozzle;
   wherein (i) the removable plate is located between a pair of flanges, (ii) each of the pair of flanges includes a sensor to generate information to send to the control module, and (iii) one of the sensors is a pressure sensor and the other sensor is a temperature sensor.

2. The steam quality measurement system of claim 1, wherein the removable plate is located upstream of the removable nozzle.

3. The steam quality measurement system of claim 1, wherein the steam quality measurement system is adapted to be inserted into an existing enhanced oil recovery system.

4. The steam quality measurement system of claim 3, wherein the steam quality measurement system is inserted between a steam generator and one or more injectors of the enhanced oil recovery system.

5. The steam quality measurement system of claim 1, wherein the removable nozzle is a converging/diverging nozzle.

6. The converging/diverging nozzle of claim 5, wherein the nozzle has a pressure drop of approximately 10% to 15%.

7. The steam quality measurement system of claim 1, wherein each respective bore of the one or more orifices is chamfered in a downstream direction.

8. The steam quality measurement system of claim 1, further comprising:
   a first sensor located upstream and proximate to the removable nozzle; and
   a second sensor located downstream and proximate to the removable nozzle in a downstream position.

9. A steam quality measurement system comprising:
   a sensor assembly including:
   an inlet adapted to receive a two-phase flow;
   a removable plate including one or more orifices each having a bore, the removable plate adapted to condition the two-phase flow;
   a removable nozzle having a bore, wherein the bore of the removable nozzle is oriented substantially parallel with each respective bore of the one or more orifices of the removable plate;
   the two-phase flow adapted to be directed through the one or more orifices and the nozzle; and
   an outlet adapted to discharge the two-phase flow;
   a control module adapted to calculate a steam quality of the two-phase flow based on receiving pressure measurements proximate the removable plate and the removable nozzle;
   wherein (i) the removable plate is located between a pair of flanges, (ii) each of the pair of the flanges includes a sensor to generate information to send to the control module, and (iii) one of the sensors is a pressure sensor and the other sensor is a temperature sensor.

10. The steam quality measurement system of claim 9, wherein the removable plate is located upstream of the removable nozzle.

11. The steam quality measurement system of claim 9, wherein the removable plate is located downstream of the removable nozzle.

12. The steam quality measurement system of claim 9, wherein the steam quality sensor assembly includes a flange assembly located proximate the removable nozzle.

13. The steam quality measurement system of claim 9, wherein (i) a first sensor is located upstream of the removable nozzle, (ii) a second sensor is located downstream of the removable nozzle, and (iii) the first sensor and the second sensor are each located proximate the removable nozzle.

14. A steam quality measurement system for an enhanced oil recovery system, the steam quality measurement system comprising:
   a pipe assembly including:
   an inlet adapted to receive a two-phase flow;
   a conditioning orifice plate located between a pair of flanges, each of the pair of flanges including a sensor;
   wherein one of the sensors is a temperature sensor and the other sensor is a pressure sensor;
   a converging/diverging nozzle;
   a flange assembly including a first flange mated to a second flange, the flange assembly being located proximate the converging/diverging nozzle; and
   an outlet adapted to discharge the two-phase flow;
   a control module adapted to calculate a steam quality of the two-phase flow based on receiving pressure and temperature measurements proximate the removable plate and the removable nozzle.

15. The pipe assembly of claim 14, wherein the conditioning orifice plate is located upstream of the converging/diverging nozzle and the flange assembly.

16. The pipe assembly of claim 14, wherein the converging/diverging nozzle and the flange assembly are located upstream of the conditioning orifice plate.

* * * * *